Figure 1:
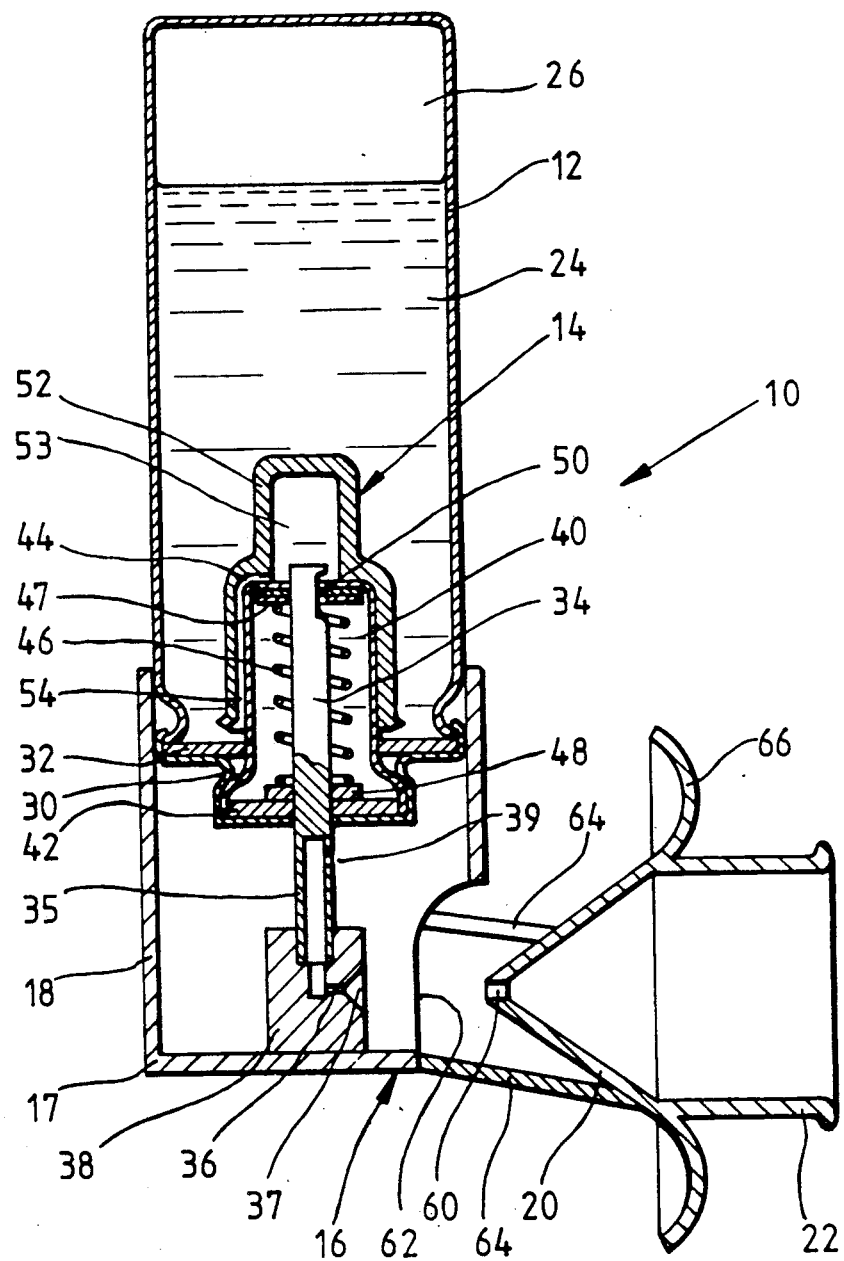

United States Patent [19]
Pritchard

[11] Patent Number: 5,048,729
[45] Date of Patent: Sep. 17, 1991

[54] AEROSOL DISPENSER WITH FLOW DIVERTER

[75] Inventor: John N. Pritchard, West Hanney, United Kingdom

[73] Assignee: United Kingdom Atomic Energy Authority, London, England

[21] Appl. No.: 550,486

[22] Filed: Jul. 10, 1990

[30] Foreign Application Priority Data

Aug. 3, 1989 [GB] United Kingdom ............... 8917775

[51] Int. Cl.$^5$ ........................................... A61M 11/00
[52] U.S. Cl. ............................. 222/402.1; 222/402.2; 128/200.23
[58] Field of Search ............. 222/402.1, 402.2, 402.12; 128/200.14, 200.18, 200.23; 239/343, 370, 371, 372, 504, 524

[56] References Cited

U.S. PATENT DOCUMENTS

| | | | |
|---|---|---|---|
| 3,838,686 | 10/1974 | Szelrely | 128/200.18 |
| 4,174,712 | 11/1979 | Moren et al. | 128/173 R |
| 4,819,834 | 4/1989 | Thiel | 222/402.2 |
| 4,940,051 | 7/1990 | Lankinen | 128/200.18 |

FOREIGN PATENT DOCUMENTS 830427 3/1960 United Kingdom .
1015882 1/1966 United Kingdom .

OTHER PUBLICATIONS

"Design of a Multistage Virtual Impactor," V. J. Novick and J. L. Alvarez, Aerosol Science and Technology, 6:63–70 (1987), Elsevier Science Publishing Co., Inc.

Primary Examiner—Michael S. Huppert
Assistant Examiner—Philippe Derakshani
Attorney, Agent, or Firm—William R. Hinds

[57] ABSTRACT

An aerosol dispenser, for example an inhaler, consists of a container (12) containing a propellant and a medicament, with a valve (14), and an applicator (16). The applicator includes a frusto-conical diverter (20) with a small orifice (60) facing the valve orifice (37). Aerosol droplets predominantly pass through the small orifice, decelerate, and can then be inhaled, while the propellant gas is predominantly diverted out of the applicator.

6 Claims, 1 Drawing Sheet

AEROSOL DISPENSER WITH FLOW DIVERTER

This invention relates to an aerosol dispenser and particularly but not exclusively an aerosol inhaler, that is a device for dispensing a medicament or therapeutic agent in the form of an aerosol to be inhaled by a patient or user.

Such inhalers are customarily used in the treatment of asthma and of hay-fever. Known inhalers comprise a container with a valve, the container containing a medicament and a liquefied propellant gas, and the valve being such that when it is depressed by the user, a fine mist or aerosol of droplets of the medicament is emitted. The droplets are then inhaled. One such inhaler, in which the valve is arranged to emit a metered dose of the medicament, is described in UK Patent GB 830 427 (Riker Labs. Inc.). A problem with known inhalers is that the droplets are emitted at a very high velocity, which may exceed 40 m/s, and so tend to impact on the back of the throat rather than being carried with inhaled air into the lungs.

According to the present invention there is provided an aerosol dispenser including an aerosol-emitting valve and an applicator through which aerosol droplets pass after emission, the applicator comprising a frusto-conical diverter defining at one end a small orifice aligned facing the valve, such that in use the aerosol droplets predominantly pass through the orifice while the gas stream entraining the droplets predominantly is diverted by the diverter.

The droplets pass through the orifice due to their momentum, and are then in a region of still air in which they soon lose their high velocity. The dispenser may be an inhaler, in which case in use the other end of the applicator would be adjacent to a user's mouth. If the user inhales air within the applicator, the droplets are carried along with the air into the lungs as desired.

Desirably the applicator also includes a shield or guard to deflect the diverted gas stream from the user's face, so it is deflected to a direction at least 90 degrees from the direction followed by the undiverted aerosol droplets.

The dimensions of the applicator are preferably such that the gas stream through the orifice is less than 10 percent, desirably less than 5 percent, of the emitted gas stream. The exact dimensions depend upon the size of the droplets which it is desired to inhale, as the smallest droplets will be carried away with the predominant gas stream.

The invention will now be further described, by way of example only, and with reference to the accompanying drawing, which shows an aerosol inhaler 10. The inhaler 10 includes a container 12 with a dose-metering valve 14; and an applicator 16 including a cap 17 and sleeve 18, a diverter 20 and a mouthpiece 22, integral with each other. The container 12 contains a solution or a suspension of an active therapeutic agent in a liquid 24 consisting principally of a propellant comprising a 70/30% mixture of dichlorodifluoromethane and trichlorofluoromethane, which also provides a vapour phase 26, and which maintains a vapour pressure typically between about 2 and 4 atmospheres. It will be appreciated that other propellants may be used.

Sealed to the container 12 by an annular gasket 32, is a lid portion 30 which supports the dose-metering valve 14, a valve stem 34 protruding through the centre of the lid portion 30. The outer portion 35 of the valve stem 34 is hollow and mates with a stepped recess in an end piece 38 fixed inside the lid 17, so as to communicate through a narrow orifice 36 (of diameter 0.5 mm) with a conical expansion orifice 37 defined in the end-piece 38. A small hole 39 is provided through the wall of the hollow portion 35. Above the lid portion 30 (as shown) is a generally cylindrical metering chamber 40. The valve stem 34 extends through the chamber 40, passing through a diaphragm seal 42 adjacent the lid portion 30 and through a metering chamber seal 44 at the upper end of the chamber 40. The seals 42 and 44 permit the valve stem 34 to slide up or down, and the stem 34 is resiliently biassed into the position shown by a compression spring 46 within the chamber 40 acting between a washer 47 adjacent the seal 44 and a flange 48 fixed to the valve stem 34. The valve stem has a groove 50 on one side near its upper end, which in the position shown provides fluid communication through the seal 44 and the washer 47 to the inside of the chamber 40. A retaining cup 52 fits tightly around the outside of the chamber 40, defining a chamber 53 into which the upper end of the valve stem 34 moves when the stem is pressed up. The chamber 53 communicates with the bottom (as shown) of the container 12 through one or more passages 54 defined by grooves in the inside wall of the cup 52.

The applicator 16 is removable from the container 12 and its valve 14. The two parts of the inhaler 10 are assembled by carefully sliding the sleeve 18 over the lid portion 30, until the hollow portion 35 of the valve stem 34 mates with the recess in the end piece 38. The diverter 20 is of frusto-conical shape, defining a small orifice 60 of diameter about 2 mm facing the expansion orifice 37. Parts of the sleeve 18 and the cap 17 are cut away to define an aperture 62 for aerosol emitted from the orifice 37, and the diverter 20 is joined to the sleeve 18 and the cap 17 by three equally-spaced thin stays 64 (only two are shown) so that the distance from the expansion orifice 37 to the small orifice 60 is about 25 mm. The wider end of the diverter 20 joins to the mouthpiece 22, which is cylindrical and coaxial with the diverter 20, and around the wider end of the diverter 20 there is also a curved annular baffle or shield 66.

As shown, the metering chamber 40 is full of the liquid 24, communicating as it does with the container 12 via the passages 54, the chamber 53, and the valve groove 50. When the inhaler 10 is to be used, the user places the mouthpiece 20 in his mouth and pushes the container 12 downwardly relative to the applicator 16. The valve stem 34 consequently slides up into the chamber 53, so the seal 44 prevents communication between the chambers 53 and 40. Then, once the small hole 39 is above the seal 42, the contents of the metering chamber 40 flow through the hollow portion 35, the narrow orifice 36 and the expansion orifice 37, as the propellant evaporates. A fine spray or aerosol of droplets of the active agent consequently emerges at high speed towards the diverter 20.

When this aerosol impinges on the diverter 20, the propellant gases are diverted to flow outside it, and are then deflected away from the user's face by the baffle 66. The droplets on the other hand, due to their momentum, continue substantially along their initial trajectories, so passing through the small orifice 60 into the relatively calm air inside the diverter 20 and the mouthpiece 22. Here they rapidly decelerate. The user then breathes in the air within the diverter 20 and the mouthpiece 22, so inhaling the droplets.

It will be appreciated that the detailed features of the valve 14 are not an aspect of the present invention, and that the applicator 16 could be used with containers with different types of valve mechanism, for example those used the other way up and provided with a dip tube instead of the retaining cap 52. It will also be appreciated that the shape and size of the diverter 20 and the small orifice 60, and its separation from the expansion orifice 37, might differ from those described here. It will be understood that the applicator 16 can be used with aerosol containers for non-medical aerosols.

I claim:

1. An aerosol dispenser including an aerosol-emitting valve and an applicator through which aerosol droplets pass after emission, the applicator comprising a frusto-conical diverter defining at one end a small orifice aligned facing the valve, such that in use the aerosol droplets predominantly pass through the orifice while the gas stream entraining the droplets predominantly is diverted by the diverter.

2. An aerosol dispenser as claimed in claim 1 wherein the applicator also comprises a shield arranged such that in use the diverted gas stream is deflected to a direction at least 90 degrees form the direction followed by the undiverted aerosol droplets.

3. An aerosol dispenser as claimed in claim 1 wherein the dimensions of the applicator are such that in use the gas stream through the orifice is less than ten percent of the emitted gas stream.

4. An aerosol dispenser as claimed in claim 3 wherein the dimensions of the applicator are such that in use the gas stream through the orifice is less than five percent of the emitted gas stream.

5. An aerosol dispenser as claimed in claim 1 wherein the applicator also comprises means to define an open-ended chamber further from the valve than the diverter, into which the orifice communicates.

6. An aerosol dispenser as claimed in claim 5 wherein the chamber is of cylindrical form, and is coaxial with the longitudinal axis of the diverter.

* * * * *